United States Patent [19]

Nishikata

[11] Patent Number: 5,917,012

[45] Date of Patent: Jun. 29, 1999

[54] PEPTIDE DERIVATIVES

[75] Inventor: Makoto Nishikata, Sapporo, Japan

[73] Assignee: Wako Pure Chemical Industries, Ltd., Osaka, Japan

[21] Appl. No.: 09/070,756

[22] Filed: Apr. 30, 1998

[30] Foreign Application Priority Data

Apr. 3, 1997 [JP] Japan ..................................... 9-126463

[51] Int. Cl.⁶ .............................. C09F 1/00; A61K 38/00; C07K 5/00; C07K 7/00
[52] U.S. Cl. .......................... 530/227; 530/328; 530/329; 530/402; 514/7; 514/15; 514/16
[58] Field of Search ..................................... 530/327, 227, 530/345, 402, 328, 329; 514/15, 16, 7

[56] References Cited

U.S. PATENT DOCUMENTS

| | | | |
|---|---|---|---|
| 5,256,677 | 10/1993 | Sham et al. .............................. | 514/351 |
| 5,387,527 | 2/1995 | Sternberg ................................. | 436/518 |

OTHER PUBLICATIONS

J. Michael Bishop, "Molecular Themes In Oncogenesis" (Cell, vol. 64, pp. 235–248, published Jan. 25, 1991).

Hyeongjin Cho, et al., "Purification and Characterization of a Soluble Catalytic Fragment of the Human Transmembrane Leukocyte Antigen Related (LAR) Protein Tyrosine Phosphatase from an *Escherichia coli* Expression System" (Biochemistry, 30, pp. 6210–6216, published 1991).

Zhizhuang Zhao, et al., "Continuous Spetrophotometric Assay of Protein Tyrosine Phosphatase Using Phosphotyrosine" (Analytical Biochemistry, 202, pp. 361–366, published 1992).

Nicholas K. Tonks, et al., "Purification of the Major Protein–tyrosine–phosphatases of Human Placenta" (The Journal of Biological Chemistry, vol. 263, p. 67226730, published May 15, 1988).

*Primary Examiner*—Avis M. Davenport
*Attorney, Agent, or Firm*—Dike, Bronstein, Roberts & Cushman, LLP; David G. Conlin

[57] ABSTRACT

Disclosed are a peptide derivative, which may be protected, containing a fluorescent group whose fluorescence is quenched with a quenching group in its molecule, the quenching group and a phosphoric acid group existing between said fluorescent group and said quenching group, in its molecule, a method for measuring protein phosphatase activity using the same as a substrate, and a reagent therefor.

10 Claims, 5 Drawing Sheets

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:1:

Gly Asp Ala Glu Tyr Ala Ala Lys Arg
1             5

(2) INFORMATION FOR SEQ ID NO:2:

(i) SEQUENCE CHARACTERISTICS:
      (A) LENGTH: 8 amino acids
      (B) TYPE: amino acid
      (D) TOPOLOGY: linear (ii) MOLECULE TYPE: peptide (xi) SEQUENCE DESCRIPTION: SEQ ID NO:2:

Gly Glu Gly Thr Tyr Gly Lys Arg
1             5

(2) INFORMATION FOR SEQ ID NO:3:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:3:

Gly Glu Val Asn Tyr Glu Glu Lys Arg
1               5

(2) INFORMATION FOR SEQ ID NO:4:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:4:

Gly Glu Pro Gln Tyr Gln Pro Lys Arg
1               5

(2) INFORMATION FOR SEQ ID NO:5:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:5:

Gly Glu Lys Glu Tyr His Ala Lys Arg
1               5

(2) INFORMATION FOR SEQ ID NO:6:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (xi) SEQUENCE DESCRIPTION: SEQ ID NO:6:

Gly Asp Gly Val Tyr Ala Ala Lys Arg
1               5

(2) INFORMATION FOR SEQ ID NO:7:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:7:

Gly Ser Ala Tyr Gly Lys Arg
1               5

(2) INFORMATION FOR SEQ ID NO:8:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:8:

Gly Gly Ser Tyr Ser Lys Arg
1               5

(2) INFORMATION FOR SEQ ID NO:9:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:9:

Gly Arg Val Phe Ser Lys Arg
1               5

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:10:

Gly Asp Arg Phe Thr Lys Arg
1               5

(2) INFORMATION FOR SEQ ID NO:11:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:11:

Gly Arg Lys Phe Thr Lys Arg
1               5

(2) INFORMATION FOR SEQ ID NO:12:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:12:

Gly Arg Lys Phe Thr Lys Arg
1               5

(2) INFORMATION FOR SEQ ID NO:13:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:13:

```
Gly Pro Gly Phe Ser Lys Arg
1               5

(2) INFORMATION FOR SEQ ID NO:14:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:14:

Gly Thr Arg Phe Ser Lys Arg
1               5
```

PEPTIDE DERIVATIVES

FIELD OF THE INVENTION

The present invention relates to peptide derivatives useful for the measurement of protein phosphatase activity, and methods for measuring protein phosphatase activity using the peptide derivative as a substrate.

BACKGROUND OF THE INVENTION

The phosphorylation of proteins by protein kinases plays an important role in the signal transduction between cells and the control of cell proliferation and differentiation (J. M. Bishop, Cell, 64, 235–248 (1991)). This reaction is reversibly controlled by the protein phosphatase-catalyzed dephosphorylation reaction. Accordingly, it is important to study protein phosphatases as well as to study protein kinases.

For the study of protein phosphatases, substrates and methods for measuring its activity are necessary. Substrates and measuring methods which have hitherto been used are as follows:

1) Using a phosphorylated amino acid-containing peptide derivative as a substrate, the release of phosphate by the action of a protein phosphatase is determined by colorimetry (H. Cho et al., Biochemistry, 30, 6210–6216 (1991)). The detection limit of phosphate by this method is about 1 nanomole. This method has a drawback that endogenous phosphate in the enzyme samples hinders the assay.

2) Using a phosphorylated amino acid-containing peptide derivative as a substrate, the absorbance or the fluorescence intensity increasing with the dephosphorylation by the action of a protein phosphatase is measured (Z. Zhao et al., Analytical Biochemistry, 201, 361–366 (1992)). The detection limit of phosphate according to this method is about 1 nanomole for the absorbance method, and about 10 picomoles for the fluorescence method. In the measurement of living samples, accurate measurement is hardly possible because of many kinds of ingredients contained therein.

3) Using a peptide derivative or a protein labelled with radioactive phosphoric acid as a substrate, the radioactivity of phosphate released by the action of a protein phosphatase is measured (N. K. Tonks et al., J. Biological Chemistry, 263, 6722–6730 (1988)). Using radioactive phosphoric acid having the specific activity of 1,000 counts per minute per picomole, the detection limit of phosphate according to this method is about 0.1 picomole. This method has the advantage that slight enzyme activity can be measured because of its high detection sensitivity. However, it has the disadvantage that the preparation of the substrate is complicated and the substrate can not be stored for a long period of time because of the decay of the radioactivity.

As described above, each of the methods for measuring protein phosphatase activity which have hitherto been employed has its merits and demerits, and hence is not necessarily satisfactory. Therefore, the development of measuring methods which are easy, high in accuracy and safe without use of radioactive substances has been desired.

SUMMARY OF THE INVENTION

It is therefore an object of the present invention to provide peptide derivatives useful as substrates for the measurement of protein phosphatase activity.

Another object of the present invention is to provide methods for measuring protein phosphatase activity using the same as a substrate.

A further object of the present invention is to provide reagents therefor.

Other and further objects of this invention will be apparent from the following description.

The present invention provides a peptide derivative, which may be protected, containing a fluorescent group whose fluorescence is quenched with a quenching group in its molecule, the quenching group and a phosphoric acid group existing between said fluorescent group and said quenching group, in its molecule; a method for measuring protein phosphatase activity using the same as a substrate; and a reagent therefor.

As a result of intensive investigation for attaining the above-mentioned objects, the present inventors have discovered that the use of the above-mentioned peptide derivative as a substrate keeps quenching of its fluorescence with the quenching group until dephosphorylation, but develops the fluorescence by allowing a proper protease to react with a dephosphorylated peptide derivative which is obtained from the above-mentioned peptide derivative by dephosphorylation to separate said fluorescent group from said quenching group, and that the use of the fluorescence intensity thereof makes it possible to measure protein phosphatase activity easily with high accuracy, thus completing the present invention.

DESCRIPTION OF THE PREFERRED EMBODIMENTS

Figure 1:
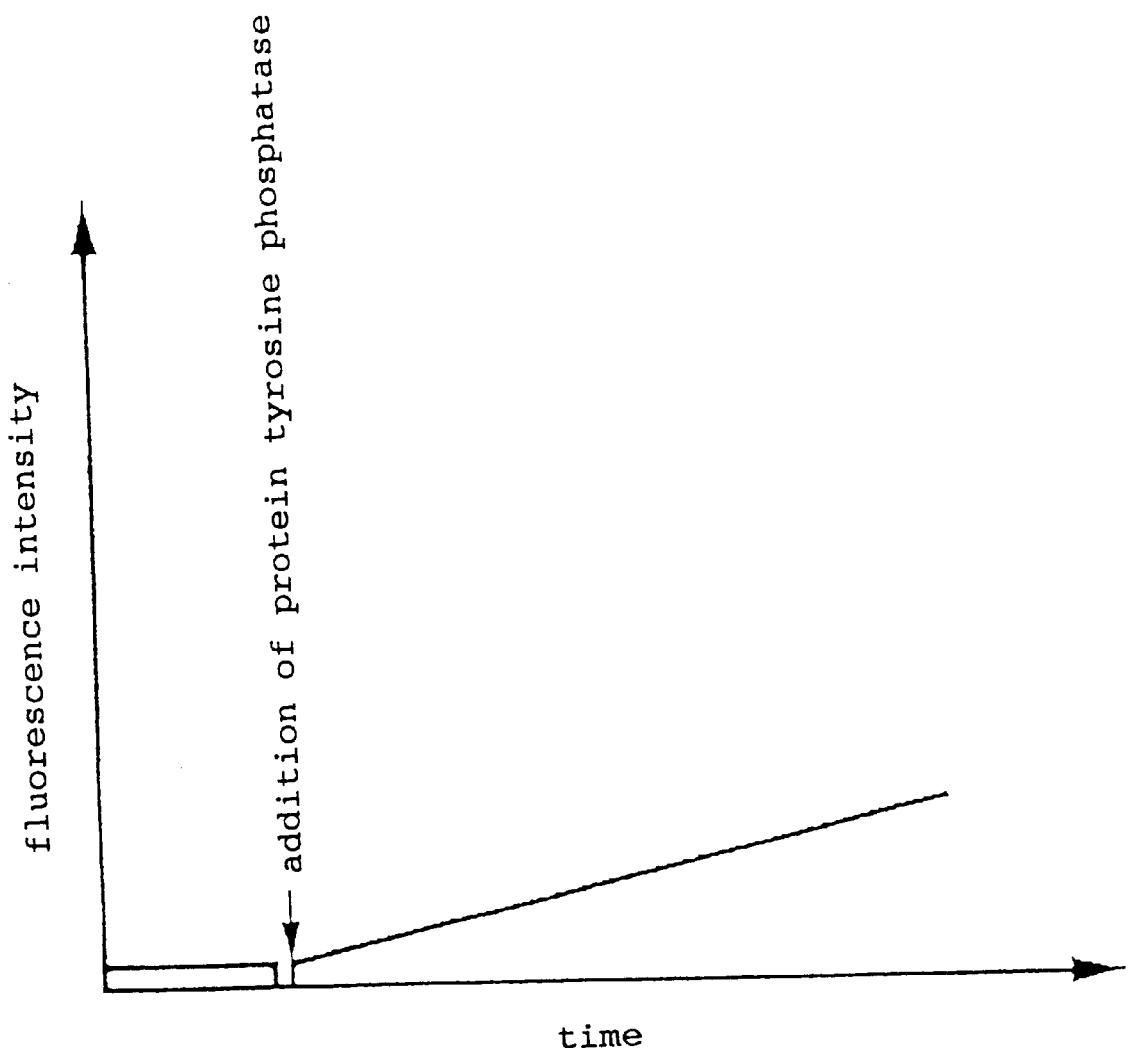
FIG. 1 is a graph showing a change in fluorescence intensity based on protein tyrosine phosphatase activity obtained by using a substrate of the present invention in Example 6.

There is no particular limitation on the fluorescent group used in the present invention, as long as it develops fluorescence when it exists under normal conditions but its fluorescence is quenched with the quenching group in the molecule, although it varies depending on the kind of quenching group present in its molecule. Specifically, examples of the fluorescent groups include a (7-methoxycoumarin-4-yl)acetyl group, a 5-[(2-aminoethyl)amino]-naphthalene-1-sulfonic acid group, a 9,10-dioxa-syn-3,4,6,7-tetramethylbimane group, etc. Each of these fluorescent groups may be appropriately bound, by conventional methods, to an α-amino group or an α-carboxyl group of a terminal amino acid, or to a side chain of an amino acid residue via, for example, an amino group, a carboxyl group or a thiol group, depending on the kind of fluorescent group. When the fluorescent groups are bound to such groups, appropriate spacers may be used.

There is no particular limitation on the quenching group used in the present invention, as long as it has the property of quenching fluorescence due to the fluorescent group existing in the molecule. Specifically, examples of the quenching groups include a dinitrophenyl group, a 4-(4-dimethylaminophenylazo)benzoyl group, a 4-(4-dimethylaminophenylazo)sulfonyl group, etc. Each of these quenching groups may be appropriately bound, by conventional methods, to an α-amino group or an α-carboxyl group of a terminal amino acid, or to a side chain of an amino acid residue via, for example, an amino group, a carboxyl group or a thiol group, depending on the kind of quenching group. When the quenching groups are bound to such groups, appropriate spacers may be used.

The peptide derivatives of the present invention include those represented by the following general formula [1]:

$$A_1—X—A_2 \qquad [1]$$

wherein X represents an amino acid residue into which a phosphoric acid group is introduced; and $A_1$ and $A_2$ each represents an amino acid residue or a peptide chain which is bound to X and may be protected, one of $A_1$ and $A_2$ having a quenching group at its terminus or a side chain thereof, and the other having a fluorescent group, at its terminus or a side chain thereof the fluorescence in the fluorescent group being quenched with the quenching group in the molecule of the peptide.

The quenching group-containing amino acid residue represented by $A_1$ or $A_2$ in general formula [1] may be protected, and is not particularly limited, as long as it is an amino acid residue which has no phosphoric acid group and no fluorescent group and to which a quenching group is bound. Further, the quenching group-containing peptide chain may be any one, as long as it comprises an amino acid residue containing the quenching group-containing amino acid residue as described above and having no phosphoric acid group and no fluorescent group. When $A_1$ or $A_2$ represents the peptide chain, there is no particular limitation on the position of the quenching group-containing amino acid residue. Although the number of the amino acid residues contained in the peptide chain is not particularly limited, it is preferably 2 to 20, including the number of the quenching group-containing amino acid residues, more preferably 2 to 10, and most preferably 2 to 5.

The fluorescent group-containing amino acid residue represented by $A_1$ or $A_2$ in general formula [1] may be protected, and is not particularly limited, as long as it is an amino acid residue which has no phosphoric acid group and no quenching group and to which a fluorescent group is bound. Further, the fluorescent group-containing peptide chain may be any one, as long as it comprises an amino acid residue containing the fluorescent group-containing amino acid residue as described above and having no phosphoric acid group and no quenching group. When $A_1$ or $A_2$ represents the peptide chain, there is no particular limitation on the position of the fluorescent group-containing amino acid residue. Although the number of the amino acid residues contained in the peptide chain is not particularly limited, it is preferably 2 to 20, including the number of the quenching group-containing amino acid residues, more preferably 2 to 10, and most preferably 2 to 5.

The peptide derivatives of the present invention may be protected, and the protecting groups include carboxyl terminal protecting groups and amino terminal protecting groups. There is no particular limitation on the carboxyl terminal protecting groups. Specifically, examples thereof include lower alkoxy groups such as methoxy, ethoxy and t-butoxy, and aromatic hydrocarbon groups such as benzyl and pentamethyl-dihydrobenzofuranyl. The terminal carboxyl group may be converted to an amido group to protect the peptide from the action of carboxypeptidases which possibly be present in an organism-derived sample. Examples of the amino terminal protecting groups include but are not limited to, t-butoxycarbonyl, benzyloxycarbonyl, 9-fluorenylmethyloxycarbonyl, 2-phenyl-2-propyl and acetyl groups.

The amino acid residues represented by X in general formula [1] include, for example, phosphorylated amino acid residues having hydroxyl groups at their side chains such as phosphorylated tyrosine, phosphorylated serine and phosphorylated threonine residues.

The amino acid sequence of the peptide derivative of the present invention may be any one, as long as it attains the objects of the present invention. More specifically, it may be appropriately selected depending on the kind of protein phosphatase to be measured and the kind of protease which is used for selectively cleaving a peptide bond between the fluorescent group-containing amino acid residue and the quenching group-containing amino acid residue. Further, although the total number of the amino acid residues contained in the peptide derivative of the present invention is not particularly limited, it is appropriately selected usually from the range of 3 to 42, preferably from the range of 3 to 22, and more preferably from the range of 3 to 12.

More specifically, the peptide derivative of the present invention may be any one obtained by replicating an appropriate range of a naturally occurring protein containing a region to be phosphorylated with a protein kinase. As described above, the replicated product of the naturally occurring protein may be used as it is. However, it is desirable to use the replicated product after appropriate modification.

That is to say, for example, when chymotrypsin selectively cleaving the carboxyl terminal side of an aromatic ring-containing amino acid residue such as a tyrosine residue is used as the protease, it is necessary to contain a phosphorylated tyrosine residue in the peptide derivative of the present invention. However, it is preferred that the peptide derivatives do not contain, in addition to the phosphorylated tyrosine, amino acid residues possibly susceptible to chymotrypsin such as tyrosine, tryptophan, phenylalanine, leucine, isoleucine, asparagine, threonine, methionine, glutamine and valine residues, particularly tyrosine, tryptophan, phenylalanine, leucine and isoleucine residues. When the natural type peptide contains such amino acid residues, it is desirable to incorporate amino acid residues which are hardly susceptible to chymotrypsin, such as an alanine residue, in place of these amino acid residues.

In the peptide derivative of the present invention, the presence of too many amino acid residues between the quenching group-containing amino acid residue and the fluorescent group-containing amino acid residue results in a weak quenching function of the quenching group. Therefore, the number of the amino acid residues present between the quenching group-containing amino acid residue and the fluorescent group-containing amino acid residue is preferably 1 to 40, more preferably 1 to 20, and most preferably 1 to 10.

The amino acid sequence of the peptide derivative of the present invention is such one that the phosphoric acid group introduced in the amino acid residue represented by X is removed by a protein phosphatase and, after this removal, one of the peptide bonds between the quenching group-containing amino acid residue and the fluorescent group-containing amino acid residue is selectively cleaved by a protease. The protein phosphatase for this purpose includes protein tyrosine phosphatase, protein serine phaophatase, protein threonine phosphatase, etc. and the protease for this purpose includes chymotrypsin, trypsin, papain, plasmin, etc., and a suitable combination of the protein phosphatase and the protease is selected, depending upon the kind of phosphoric acid group-containing amino acid residue and other conditions.

Typical examples of the peptide derivatives of the present invention, which comprise the amino acid sequence mentioned above, are as shown below.

Flu-Gly-Asp-Ala-Glu-pTyr-Ala-Ala-Lys(Inh)-Arg-NH$_2$
Flu-Gly-Glu-Gly-Thr-pTyr-Gly-Lys(Inh)-Arg-NH$_2$
Flu-Gly-Glu-Val-Asn-pTyr-Glu-Glu-Lys(Inh)-Arg-NH$_2$
Flu-Gly-Glu-Pro-Gln-pTyr-Gln-Pro-Lys(Inh)-Arg-NH$_2$
Flu-Gly-Glu-Lys-Glu-pTyr-His-Ala-Lys(Inh)-Arg-NH$_2$
Flu-Gly-Asp-Gly-Val-pTyr-Ala-Ala-Lys(Inh)-Arg-NH$_2$
Flu-Gly-Ser-Ala-pTyr-Gly-Lys(Inh)-Arg-NH$_2$
Flu-Gly-Gly-Ser-pTyr-Ser-Lys(Inh)-Arg-NH$_2$
Flu-Gly-Arg-Val-Phe-pSer-Lys(Inh)-Arg-NH$_2$
Flu-Gly-Asp-Arg-Phe-pThr-Lys(Inh)-Arg-NH$_2$
Flu-Gly-Arg-Lys-Phe-pThr-Lys(Inh)-Arg-NH$_2$
Flu-Gly-Pro-Gly-Phe-pSer-Lys(Inh)-Arg-NH$_2$
Flu-Gly-Thr-Arg-Phe-pSer-Lys(Inh)-Arg-NH$_2$
Flu-Gly-Lys-Arg-Phe-pSer-Lys(Inh)-Arg-NH$_2$ wherein Flu represents a fluorescent group, pTyr represents an O-phosphotyrosine residue, pSer represents an O-phosphoserine residue, pThr represents an O-phosphothreonine residue, Inh represents a quenching group, Lys(Inh) represents a lysine residue to which a quenching group is bound, and other abbreviations are the abbreviations of amino acid residues commonly used in the art.

The peptide derivative of the present invention can be synthesized using the fluorescent group-containing amino acids and the quenching group-containing amino acids as starting materials by post-phosphorylation or pre-phosphorylation which is a conventional method in the synthesis of peptides containing phosphorylated amino acid residues. The post-phosphorylation is a method in which hydroxyamino acid residues are phosphorylated after construction of peptides, and the pre-phosphorylation is a method in which a protected phosphoaminq acid derivative previously synthesized is incorporated into a peptide chain as a building block. Although the peptide derivatives of the present invention can be synthesized by both the above-mentioned methods, the pre-phosphorylation is preferred, paritcularly in a case, where the peptide chains contain amino acid residues easily oxidized such as methionine, cysteine and tryptophan residues.

The methods for phosphorylating the amino acid residues include a method in which the amino acid residues to be phosphorylated are allowed to react, the amino acid residues having free hydroxyl groups, with phosphorylating agents, in an amount of 1 to 20 equivalents based on free hydroxyl groups of the amino acid residues, the phosphorylating agents being, for example, sulfonyl chloride and phosphorus halides such as phosphorus trichloride, in an anhydrous solvent such as dimethylformamide (DMF) and dimethyl sulfoxide (DMSO), in the presence of an alkaline substance such as pyridine, triethylamine and NaH as catalysts, at 0° C. to 40° C. for 1 hour to 24 hours.

Further, the peptide chains may be constructed according to conventional methods usually employed in this field. Amino acids which may be protected may be bound one by one to the carboxyl terminal side or the amino terminal side of a main chain, or several fragments separately synthesized may be bound to one another. There is no particular limitation thereon.

The activation of carboxyl groups for producing peptide bonds may be conducted by conventional methods usually employed in the art, such as the azide method, the mixed acid anhydride method, the dicyclohexylcarbodiimide method and the active ester method.

The reaction temperature is usually from −30° C. to 50° C., and preferably from −10° C. to 25° C.

The reaction time is usually from 10 minutes to 24 hours, and preferably from 30 minutes to 2 hours, although it varies depending on the synthesis method.

An example of the methods for synthesizing the peptide derivatives of the present invention is described below, using Mca-Gly (wherein Mca is a (7-methyloxycoumarin-4-yl) acetyl group) as the fluorescent group-containing amino acid, Fmoc-Tyr(PO$_3$H$_2$) (wherein Fmoc is a 9-fluorenylmethyloxycarbonyl group) as the phosphorylated amino acid, and Fmoc-Lys(DNP) (wherein DNP is a dinitrophenyl group) as the quenching group-containing amino acid.

Mca-Gly is similarly synthesized, for example, according to the method for synthesizing Mca-Pro-Leu (C. G. Knight et al., *FEBS Letters*, 296, 263–266 (1992)). As for Fmoc-Tyr(PO$_3$H$_2$), a commercially available product (for example, manufactured by Nova Biochem Co.) may be used.

Fmoc-Lys(DNP) is similarly synthesized based on the conventional method (H. Nagase et al., *Journal of Biological Chemistry*, 269, 20952–20957 (1994)). The peptide chain of the total peptide derivative of the present invention is similarly constructed by solid phase polymerization based on the method of constructing a peptide chain with a phosphoric acid group not protected (E. A. Ottinger, L. L. Shekels, D. A. Bernlohr and G. Barany, *Biochemistry*, 32, 4353–4361 (1993)). Operations and after treatment methods other than those described above may be carried out based on the methods known in the art.

The fluorescent group of the present invention itself develops fluorescence when it is bound to a normal residue, but the fluorescence is quenched in the peptide deriavatives of the present invention due to the quenching group co-existed in the derivatives. When the phosphoric acid group in the derivatives is removed by dephosphorylation and then the peptide bond is cleaved by protease between the fluorescent group-containing portion and the quenching group-containing portion, the fluorescent goup is, as a result, separated from the quenching group, i.e. the quenching group does not exist at all in the molecule or residue to which the fluorescent group is bound, and thus the original fluorescent activity of the fluorescent group is revived to develop the fluorescence.

The use of the peptide derivatives of the present invention as the substrates makes it possible to measure the activity of, for example, protein tyrosine phosphatase, protein serine phosphatase and protein threonine phosphatase contained in living samples such as the serum, the plasma and the cerebrospinal fluid.

The activity may be measured, for example, as follows.

That is to say, an appropriate buffer containing an appropriate amount of the peptide derivative of the present invention is previously incubated at an appropriate temperature, and the living sample such as the serum, the plasma or the cerebrospinal fluid is added thereto, followed by further incubation at the same temperature for 1 minute to 30 minutes. Then, a protein phosphatase inhibitor such as a solution of sodium vanadate is added thereto to terminate the enzyme reaction. To this solution a protease is added. This protease is such one which specifically cleaves one of the peptide bonds present between the quenching group-containing amino acid residue and the fluorescent group-containing amino acid group when the phosphoric acid group of the phosphorylated amino acid residue contained in the peptide derivative is removed (i.e. a dephosphorylated peptide derivative derived from the peptide derivative of the present invention is produced.). The protease exemplified by chymotrypsin, trypsin, papain or plasmin. Then, the intensity of the thus developed fluorescence is measured. The resulting fluorescence intensity is applied to a calibration curve showing the relationship between the fluorescence intensity and the protein phosphatase activity determined by the same operation as described above with the exception that a protein phosphatase solution having a previously known concentration is used as a sample, thereby enabling the determination of the protein phosphatase activity in the sample.

Although the concentration of the peptide derivative of the present invention used in this case varies depending on the degree to which the calibration range is established, it is appropriately selected usually from the range of 0.1 $\mu$M to 100 $\mu$M, and preferably from the range of 1 $\mu$M to 10 $\mu$M, as the concentration in reacting with the protein phosphatase. There is no particular limitation on the pH at the time when the protein phosphatase is allowed to react, as long as it is within the range where the protein phosphatase activity can be measured. However, it is appropriately selected usually from the range of 4 to 9, and preferably from the range of 5 to 8, and the incubation temperature is appropriately selected usually from the range of 20° C. to 40° C. Although the concentration of the protein phosphatase inhibitor somewhat varies depending on the kind of inhibitor, it is appropriately selected usually from the range of 0.01 mM to 10 mM, and preferably from the range of 0.1 mM to 1 mM, as the concentration in reacting. Although the concentration of the protease somewhat varies depending on the kind of protease, it is appropriately selected usually from the range of 0.1 $\mu$g/ml to 100 $\mu$g/ml, and preferably from the range of 1 $\mu$g/ml to 50 $\mu$g/ml, as the concentration in reacting.

When the protein phosphatase to be measured is not inactivated with the protease used, the protein phosphatase activity can also be determined by the following method.

That is to say, an appropriate buffer containing appropriate amounts of the peptide derivative of the present invention and the protease having the properties as described above is previously incubated at an appropriate temperature, and the living sample such as the serum, the plasma or the cerebrospinal fluid is added thereto. Then, a change in fluorescence intensity per unit time is determined with further incubation at the same temperature. The resulting change in fluorescence intensity is applied to a calibration curve showing the relationship between the change in fluorescence intensity and the protein phosphatase activity determined by the same operation as described above with the exception that a protein phosphatase solution having a previously known concentration is used as a sample, thereby enabling the determination of the protein phosphatase activity in the sample.

Although the concentration of the peptide derivative of the present invention used in this case varies depending on the degree to which the calibration range is established, it is appropriately selected usually from the range of 0.1 $\mu$M to 100 $\mu$M, and preferably from the range of 1 $\mu$M to 10 $\mu$M, as the concentration in reacting with the protein phosphatase. There is no particular limitation on the pH at the time when the protein phosphatase is allowed to react, as long as it is within the range that the protein phosphatase activity can be measured. However, it is appropriately selected usually from the range of 4 to 9, and preferably from the range of 5 to 8, and the incubation temperature is appropriately selected usually from the range of 20° C. to 40° C. Although the concentration of the protease somewhat varies depending on the kind of protease, it is appropriately selected usually from the range of 0.1 $\mu$g/ml to 100 $\mu$g/ml, and preferably from the range of 1 $\mu$g/ml to 50 $\mu$g/ml, as the concentration in reacting.

The measuring reagents used of the present invention comprises as the main ingredient the peptide derivatives mentioned-above, and they are used for measuring the protein phosphatase activity of the organism-derived samples such as the serum and the plasma or tissue extracts. The preferred embodiments thereof and specific examples are described above.

The reagents are available in the lyophilized state or in the solution state, and may contain additives such as surfactants, preservatives and buffers which are usually used in this field, in addition to ones described above, as long as they do not inhibit the measurements of the protein phosphatase activity. The concentration of these additives used may be appropriately selected, based on the concentration usually employed in this field.

The present invention will be described in more detail through the following examples. It is understood of course that they are not intended to limit the scope of the invention.

In the examples, the following abbreviations are used.
Fmoc: 9-Fluorenylmethyloxycarbonyl Group
Mca: (7-Methoxycoumarin-4-yl)acetyl Group
pTyr: O-Phosphotyrosine Residue
Lys(DNP): N$\epsilon$-Dinitrophenyllysine Residue
Pbf: Pentamethyldihydrobenzofuranyl Group
$^t$Bu: t-Butyl Group
PyBOP: Benzotriazole-1-yl-oxy-tris-pyrrolidinophosphonium Hexafluorophosphate
HOBt: 1-Hydroxybenzotriazole
DIEA: Diisopropylethylamine
TFA: Trifluoroacetic acid

EXAMPLE 1

Synthesis of Mca-Gly-Asp-Ala-Glu-pTyr-Ala-Ala-Lys(DNP)-Arg-NH$_2$ (A Peptide Derivative of the Present Invention)

Using Mca-Gly, Fmoc-Asp(O$^t$Bu), Fmoc-Ala, Fmoc-Glu (O$^t$Bu), Fmoc-Tyr(PO$_3$H$_2$), Fmoc-Lys(DNP) and Fmoc-Arg (Pbf) as starting materials, and PyBOP, HOBt and DIEA as binding agents, a peptide derivative was synthesized by a solid phase method based on the method of constructing a peptide chain with a phosphoric acid group not protected (E. A. Ottinger, L. L. Shekels, D. A. Bernlohr and G. Barany, *Biochemistry*, 32, 4353–4361 (1993)). That is to say, first, a DMF solution containing 10 equivalents of a predetermined protecting amino acid residue, 10 equivalents of PyBOP, 10 equivalents of HOBt and 20 equivalents of DIEA were added onto 10 mg of a 4-(2',4'-dimethoxyphenyl-Fmoc-aminomethyl)-phenoxy-acetamido-norleucylmethylbenzhydrylamine resin (manufactured by Watanabe Kagaku Kogyo Co., hereinafter referred to as an MBHA resin for brevity), and the coupling reaction was conducted at room temperature for 1 hour, thereby successively introducing the amino acid residues. The amino acid residues were introduced in the order of Fmoc-Arg(Pbf) (manufactured by Watanabe Kagaku Kogyo Co.), Fmoc-Lys (DNP) (synthesized with reference to H. Nagase et al., *Journal of Biological Chemistry*, 269, 20952–20957 (1994)), Fmoc-Ala (manufactured by Watanabe Kagaku Kogyo Co.), Fmoc-Ala, Fmoc-Tyr($PO_3H_2$) (manufactured by Nova Biochem Co.), Fmoc-Glu(O$^t$Bu) (manufactured by Watanabe Kagaku Kogyo Co.), Fmoc-Ala, Fmoc-Asp (O$^t$Bu) (manufactured by Watanabe Kagaku Kogyo Co.) and Mca-Gly (synthesized with reference to C. G. Knight et al., *FEBS Letters*, 296, 263–266 (1992)). After the reaction was completed, the MBHA resin was washed with water, and 1 ml of a mixed solution of TFA, water, thioanisole, phenol and ethanedithiol (84:5:5:3:3) was added thereto. Then, the mixture was stirred at room temperature for 2 hours to cut off the desired peptide from the resin, and at the same time, the $^t$Bu groups (the protecting groups of side chain carboxyl groups of Glu and Asp) and the Pbf group (the protecting group of a side chain guanidino group of Arg). Then, the resin was removed by filtration, and the filtrate was concentrated while blowing nitrogen gas thereon, followed by addition of ether to precipitate the desired product. The precipitates were collected and dried in a desiccator to obtain 7.0 mg (in a 97% yield) of the peptide derivative, a compound of the present invention. The amino acid analysis and the mass spectrometry revealed that the resulting peptide derivative was the desired compound.

EXAMPLE 2

Synthesis of Mca-Gly-Glu-Gly-Thr-pTyr-Gly-Lys (DNP)-Arg-$NH_2$ (A Peptide Derivative of the Present Invention)

Using Mca-Gly, Fmoc-Glu(O$^t$Bu), Fmoc-Gly, Fmoc-Thr ($^t$Bu), Fmoc-Tyr($PO_3H_2$), Fmoc-Lys(DNP) and Fmoc-Arg (Pbf) as starting materials, a peptide derivative was synthesized in the same manner as with Example 1.

As Fmoc-Gly and Fmoc-Thr($^t$Bu), products manufactured by Watanabe Kagaku Kogyo Co. were used, and the amino acid residues were introduced in the order of Fmoc-Arg (Pbf), Fmoc-Lys(DNP), Fmoc-Gly, Fmoc-Tyr($PO_3H_2$), Fmoc-Thr(O$^t$Bu), Fmoc-Gly, Fmoc-Glu($^t$Bu) and Mca-Gly.

The yield was quantitative, and the amino acid analysis and the mass spectrometry revealed that the resulting peptide derivative was the desired compound.

EXAMPLE 3

Synthesis of Mca-Gly-Asp-Gly-Val-pTyr-Ala-Ala-Lys(DNP)-Arg-$NH_2$ (A Peptide Derivative of the Present Invention)

Using Mca-Gly, Fmoc-Asp(O$^t$Bu), Fmoc-Val, Fmoc-Tyr ($PO_3H_2$), Fmoc-Ala, Fmoc-Lys(DNP) and Fmoc-Arg(Pbf) as starting materials, a peptide derivative was synthesized in the same manner as in Example 1.

As Fmoc-Val, a product manufactured by Watanabe Kagaku Kogyo Co. was used, and the amino acid residues were introduced in the order of Fmoc-Arg(Pbf), Fmoc-Lys (DNP), Fmoc-Ala, Fmoc-Ala, Fmoc-Tyr($PO_3H_2$), Fmoc-Val, Fmoc-Gly, Fmoc-Asp(O$^t$Bu) and Mca-Gly.

The yield was quantitative, and the amino acid analysis and the mass spectrometry revealed that the resulting peptide derivative was the desired compound.

EXAMPLE 4

Synthesis of Mca-Gly-Ser-Ala-pTyr-Gly-Lys(DNP)-Arg-$NH_2$ (A Peptide Derivative of the Present Invention)

Using Mca-Gly, Fmoc-Ser($^t$Bu), Fmoc-Ala, Fmoc-Tyr ($PO_3H_2$), Fmoc-Lys(DNP) and Fmoc-Arg(Pbf) as starting materials, a peptide derivative was synthesized in the same manner as in Example 1.

As Fmoc-Ser($^t$Bu), a product manufactured by Watanabe Kagaku Kogyo Co. was used, and the amino acid residues were introduced in the order of Fmoc-Arg(Pbf), Fmoc-Lys (DNP), Fmoc-Gly, Fmoc-Tyr($PO_3H_2$), Fmoc-Ala, Fmoc-Ser ($^t$Bu) and Mca-Gly.

The yield was quantitative, and the amino acid analysis and the mass spectrometry revealed that the resulting peptide derivative was the desired compound.

EXAMPLE 5

Synthesis of Mca-Gly-Gly-Ser-pTyr-Ser-Lys(DNP)-Arg-$NH_2$ (A Peptide Derivative of the Present Invention)

Using Mca-Gly, Fmoc-Gly, Fmoc-Ser($^t$Bu), Fmoc-Tyr ($PO_3H_2$), Fmoc-Lys(DNP) and Fmoc-Arg(Pbf) as starting materials, a peptide derivative was synthesized in the same manner as in Example 1.

The amino acid residues were introduced in the order of Fmoc-Arg(Pbf), Fmoc-Lys(DNP), Fmoc-Ser($^t$Bu), Fmoc-Tyr($PO_3H_2$), Fmoc-Ser($^t$Bu), Fmoc-Gly and Mca-Gly.

The yield was quantitative, and the amino acid analysis and the mass spectrometry revealed that the resulting peptide derivative was the desired compound.

EXAMPLE 6

Measurement of Protein Tyrosine Phosphatase Activity

Reagents

Substrate Solution: A 10 mM dimethyl glutarate buffer (pH 6.6) containing 1 $\mu$M of Mca-Gly-Asp-Ala-Glu-pTyr-Ala-Ala-Lys(DNP)-Arg-$NH_2$ synthesized in Example 1 was used as a substrate solution.

Chymotrypsin Solution: 1 mM hydrochloric acid (pH 3) containing 0.2% of chymotrypsin (manufactured by Sigma Inc.) was used as a chymotrypsin solution.

Protein Tyrosine Phosphatase Solution: A 10 mM dimethyl glutarate buffer (pH 6.6) containing 1 U/ml of protein tyrosine phosphatase (derived from *Yersinia enterocolitica*, manufactured by New England Biolabs Inc.) was used as a protein tyrosine phosphatase solution, wherein "1 U" is the amount of an enzyme hydrolyzing 1 nanomole of p-nitrophenyl phosphate per minute, when protein tyrosine phosphatase is added to a 20 mM dimethyl glutarate buffer (pH 6.6) containing 10 mM p-nitrophenyl phosphate and allowed to react at 25° C. (hereinafter the same).

Operating Method

To a cell for fluorometry (10 mm×10 mm), 1 ml of the substrate solution and 10 $\mu$l of the chymotrypsin solution were added, followed by incubation at 25° C. for 5 minutes. Then, 1 $\mu$l of the protein tyrosine phosphatase solution was added thereto, and the change in fluorescence intensity is measured by use of a fluorophotometer (Hitachi F-3000, excitation wavelength: 328 nm, fluorescent wavelength: 395 nm) with further incubation at 25° C.

Results

Results are shown in FIG. 1.

As apparent from FIG. 1, the results shows that the use of the peptide derivative of the present invention as the substrate permits the protein tyrosine phosphatase activity to be measured on real time with high accuracy.

EXAMPLE 7

Reagents

Sodium Vanadate Solution: Sodium vanadate was dissolved in water so as to give a concentration of 100 mM thereby forming a sodium vanadate solution.

A substrate solution, a chymotrypsin solution and a protein tyrosine phosphatase solution were the same as with Example 6.

Operating Method

To a cell for fluorometry, 1 ml of the substrate solution was added, followed by incubation at 25° C. for 5 minutes. Then, 1 µl of the protein tyrosine phosphatase solution was added thereto, followed by reaction with incubation at 25° C. for 10 minutes. Thereafter, 1 µl of the sodium vanadate solution was added thereto to inactivate protein tyrosine phosphatase, followed by addition of 10 µl of the chymotrypsin solution. Then, the change in fluorescence intensity is measured by use of a fluorophotometer (Hitachi F-3000, excitation wavelength: 328 nm, fluorescent wavelength: 395 nm).

Results

Figure 2:
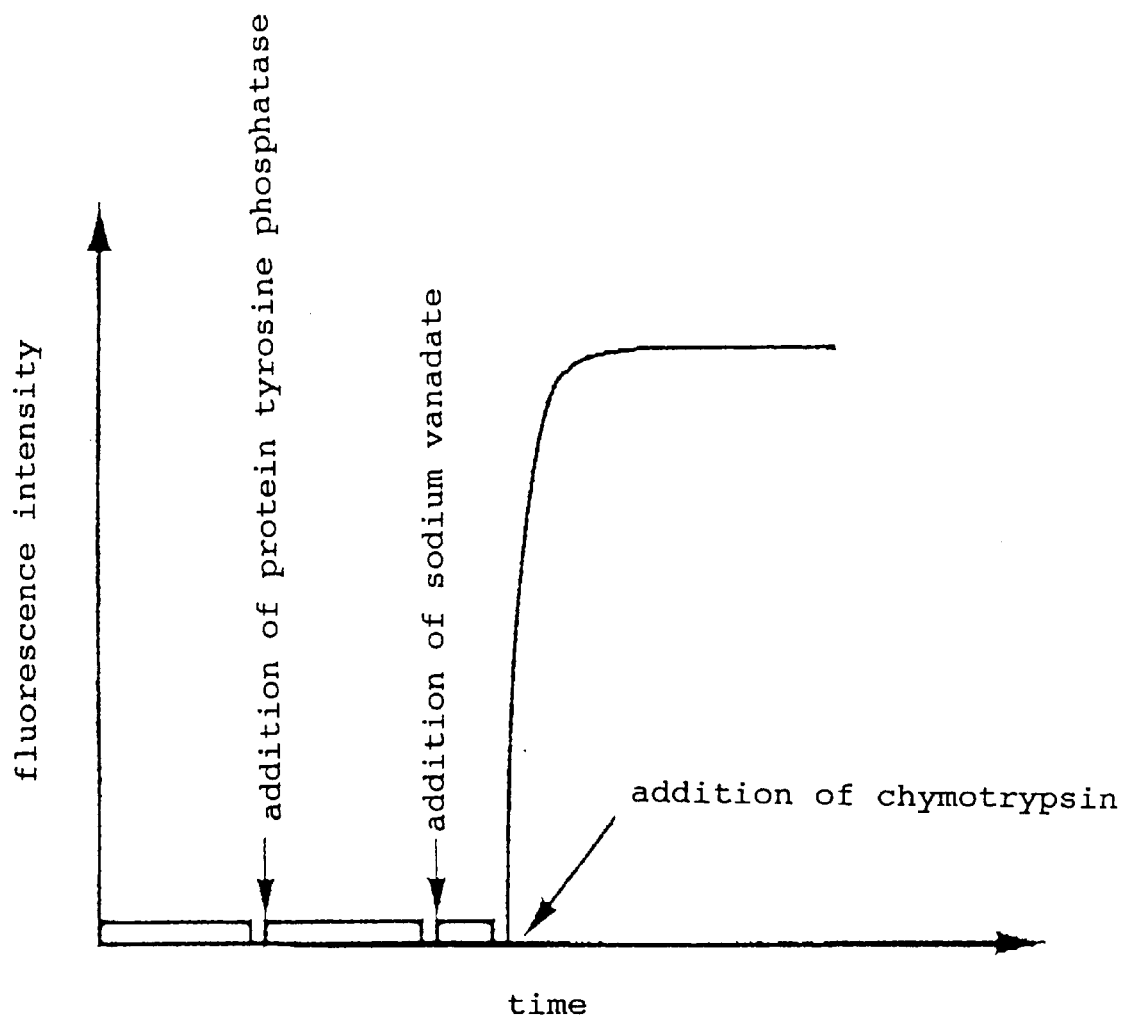
FIG. 2 is a graph showing a change in fluorescence intensity based on protein tyrosine phosphatase activity obtained by using a substrate of the present invention in Example 7.

Results are shown in FIG. 2.

As apparent from FIG. 2, the results show that the use of the peptide derivative of the present invention as the substrate provides the fluorescence intensity corresponding to the protein tyrosine phosphatase activity, in other wards, the activity can be measured with high accuracy.

EXAMPLE 8

Measurement of Protein Tyrosine Phosphatase Activity

Reagents

Substrate Solution: A 20 mM dimethyl glutarate buffer (pH 6.6) containing 1 µM of Mca-Gly-Asp-Ala-Glu-pTyr-Ala-Ala-Lys(DNP)-Arg-NH$_2$ synthesized in Example 1 was used as a substrate solution.

Chymotrypsin Solution: 1 mM hydrochloric acid (pH 3) containing 5% of chymotrypsin (manufactured by Worthington) was used as a chymotrypsin solution.

Sodium Vanadate Solution: Sodium vanadate was dissolved in water so as to give a concentration of 10 mM thereby forming a sodium vanadate solution.

Protein Tyrosine Phosphatase Solution: A 20 mM dimethyl glutarate buffer (pH 6.6) containing a predetermined unit (U) of protein tyrosine phosphatase (derived from *Yersinia enterocolitica*, manufactured by New England Biolabs Inc.) was used as a protein tyrosine phosphatase solution.

Operating Method

To a cell for fluorometry (5 mm×5 mm), 200 µl of the substrate solution was added, followed by incubation at 25° C. for 2 minutes. Then, 2 µl of the predetermined protein tyrosine phosphatase solution was added thereto, followed by reaction with incubation at 25° C. for 1 minute. Thereafter, 2 µl of the sodium vanadate solution was added thereto to inactivate protein tyrosine phosphatase, followed by addition of 2 µl of the chymotrypsin solution. Then, the change in fluorescence intensity is measured by use of a fluorophotometer (Hitachi F-3000, excitation wavelength: 328 nm, fluorescent wavelength: 395 nm).

Results

Figure 3:
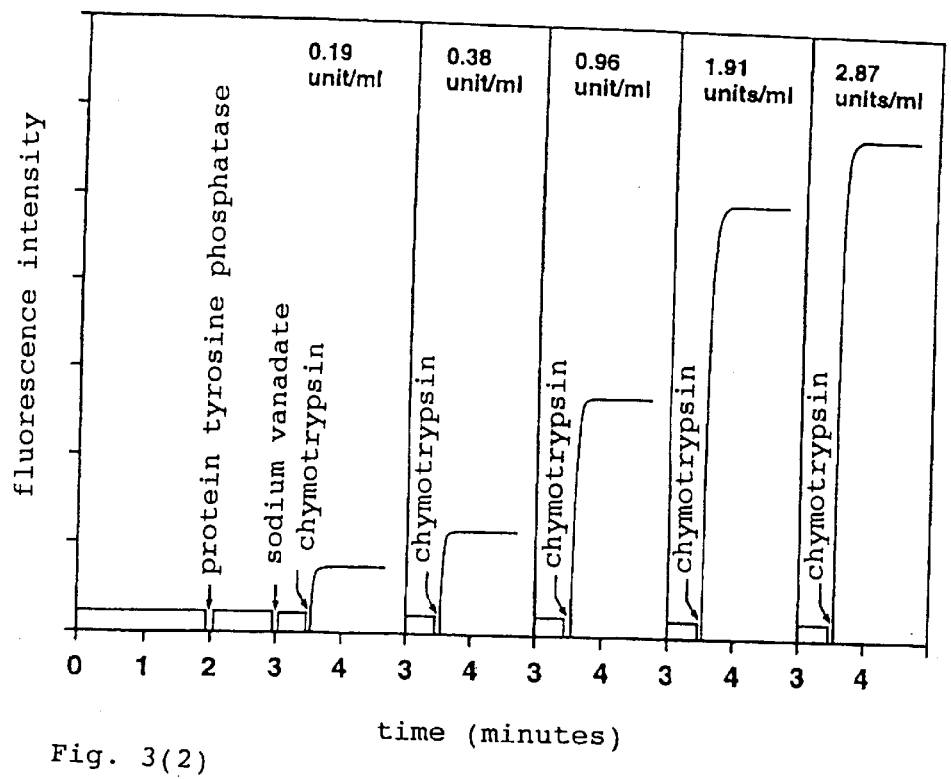
FIG. 3 (1) is a graph showing a change in fluorescence intensity based on protein tyrosine phosphatase activity obtained by using a substrate of the present invention in Example 8, and FIG. 3 (2) is a calibration curve showing the relationship between the concentration of a protein tyrosine phosphatase and the dephosphorylation rate obtained in Example 8.
Figure 3:
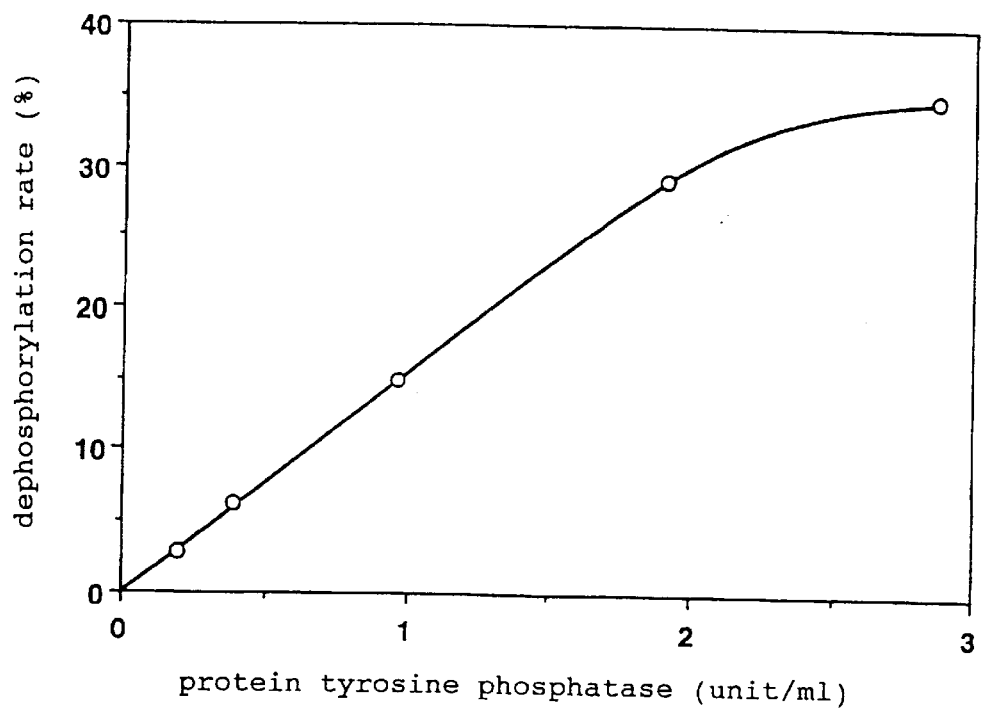

Results are shown in FIGS. 3 (1) and 3 (2).

FIG. 3 (1) shows the results of measurements of the change in fluorescence intensity, and FIG. 3 (2) is a calibration curve obtained based on the results in FIG. 3(1) and shows the relationship between the concentration (U/ml) of the protein tyrosine phosphatase solution and the dephosphorylation rate (%) determined from the change in fluorescence intensity.

These results apparently show that the use of the peptide derivative of the present invention as the substrate provides the fluorescence intensity corresponding to the concentration (U/ml) of protein tyrosine phosphatase in the sample, in other wards, the concentration can be measured with high accuracy.

EXAMPLE 9

Measurement of Protein Tyrosine Phosphatase Activity

Reagents

Substrate Solution: A 20 mM dimethyl glutarate buffer (pH 6.6) containing 2 µM of Mca-Gly-Glu-Gly-Thr-pTyr-Gly-Lys(DNP)-Arg-NH$_2$ synthesized in Example 2 was used as a substrate solution.

Chymotrypsin Solution: 1 mM hydrochloric acid (pH 3) containing 0.2% of chymotrypsin (manufactured by Worthington) was used as a chymotrypsin solution.

Protein Tyrosine Phosphatase Solution: A 20 mM dimethyl glutarate buffer (pH 6.6) containing 30 U/ml of protein tyrosine phosphatase (derived from *Yersinia enterocolitica*, manufactured by New England Biolabs Inc.) was used as a protein tyrosine phosphatase solution.

Operating Method

To a cell for fluorometry (5 mm×5 mm), 200 µl of the substrate solution and 2 µl of the chymotrypsin solution were added, followed by incubation at 25° C. for 2 minutes. Then, 1 µl of the protein tyrosine phosphatase solution was added thereto, and the change in fluorescence intensity is measured by use of a fluorophotometer (Hitachi F-3000, excitation wavelength: 328 nm, fluorescent wavelength: 395 nm) with further incubation at 25° C.

Results

Figure 4:
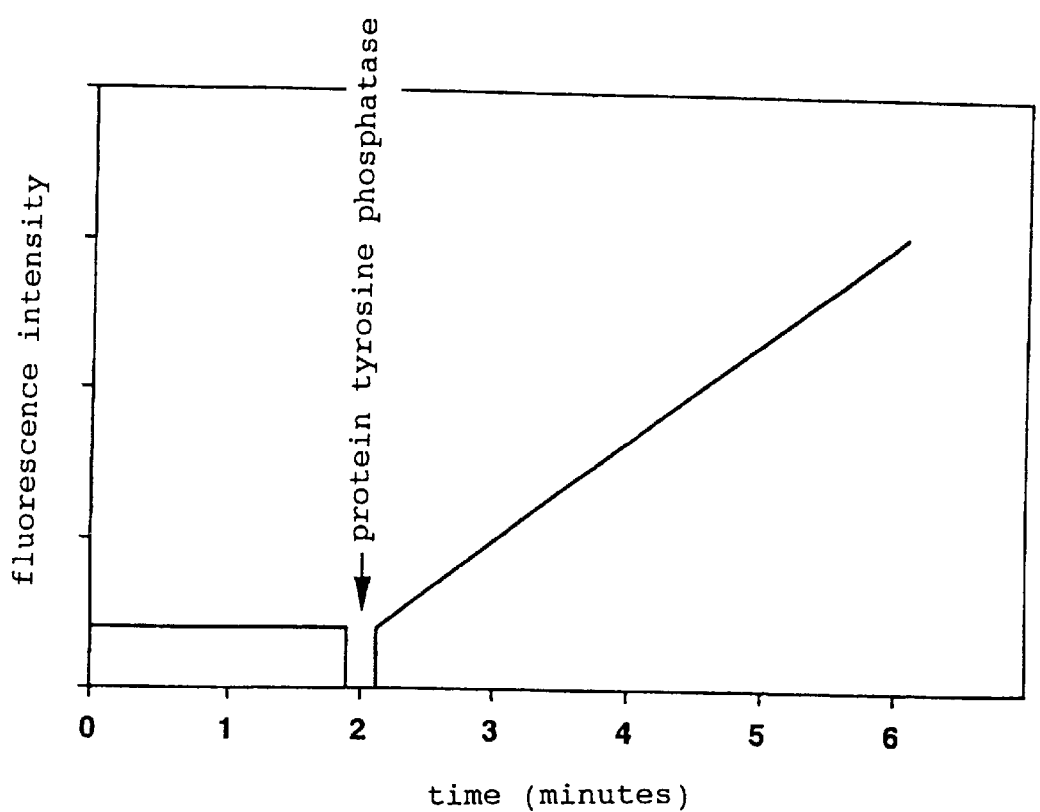
FIG. 4 is a graph showing a change in fluorescence intensity based on protein tyrosine phosphatase activity obtained by using a substrate of the present invention in Example 9.

Results are shown in FIG. 4.

As apparent from FIG. 4, the results show that the use of the peptide derivative of the present invention as the substrate permits the protein tyrosine phosphatase activity to be measured on real time with high accuracy. Further, the results also indicate that this method can become an effective means for kinetic analysis of the reaction of protein tyrosine phosphatase with the substrate.

EXAMPLE 10

Measurement of Maximum Velocity (Vmax) and Michaelis Constant (Km) of Protein Tyrosine Phosphatase Reagents Substrate Solution: A 20 mM dimethyl glutarate buffer (pH 6.6) containing a predetermined concentration of Mca- Gly-Asp-Ala-Glu-pTyr-Ala-Ala-Lys(DNP)-Arg-NH$_2$ synthesized in Example 1 was used as a substrate solution.

Chymotrypsin Solution: 1 mM hydrochloric acid (pH 3) containing 5.0% of chymotrypsin (manufactured by Worthington) was used as a chymotrypsin solution.

Protein Tyrosine Phosphatase Solution: A 20 mM dimethyl glutarate buffer (pH 6.6) containing 20 U/ml of protein tyrosine phosphatase (derived from *Yersinia enterocolitica*, manufactured by New England Biolabs Inc.) was used as a protein tyrosine phosphatase solution.

Operating Method

To a cell for fluorometry (5 mm×5 mm), 200 μl of the substrate solution and 2 μl of the chymotrypsin solution were added, followed by incubation at 25° C. for 2 minutes. Then, 1 μl of the protein tyrosine phosphatase solution was added thereto, and the change in fluorescence intensity is measured by use of a fluorophotometer (Hitachi F-3000, excitation wavelength: 328 nm, fluorescent wavelength: 395 nm) with further incubation at 25° C. From the resulting reaction time course, the initial velocities at various substrate concentrations (the change in fluorescence intensity per minute) were determined.

Results

Figure 5:
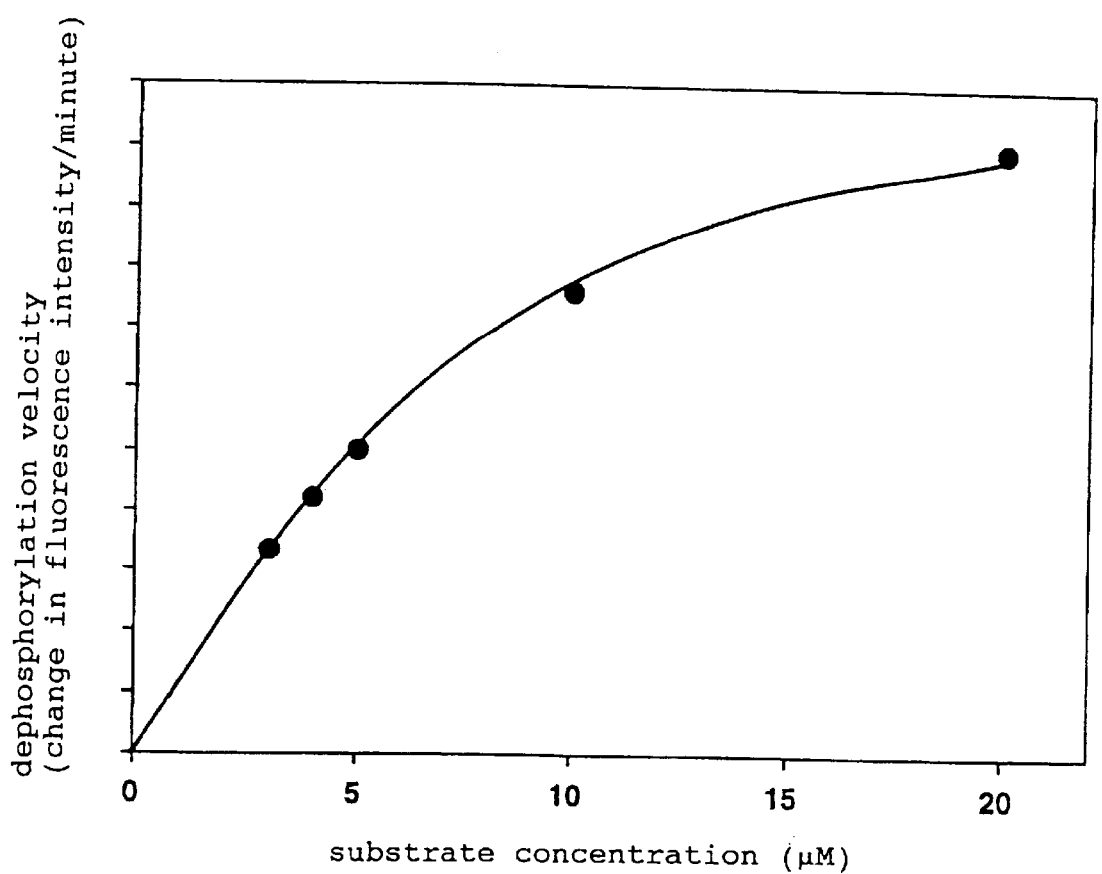
FIG. 5 is a graph showing the relationship between the substrate concentration (abscissa) and the initial velocity (ordinate) obtained at a predetermined substrate concentration, obtained in Example 10.

Results are shown in FIG. 5. FIG. 5 is a graph showing the relationship between the substrate concentration (abscissa) and the initial velocity (ordinate) obtained at the predetermined substrate concentration.

Based on the results, the maximum velocity (Vmax) and the Michaelis constant (Km) of protein tyrosine phosphatase were determined by the conventional method of this field. As a result, the following values were each obtained.

Vmax: 1.69 nmol/unit·min

Km: 11.0 μM

As apparent from the above, the kinetic studies of protein phosphatases can be easily conducted by utilizing the present invention.

As described above, the present invention provides the novel peptide derivatives, and the methods for measuring protein phosphatase activity using the same as substrates, and achieves the following significant effects to contribute greatly to this industry.

1) The measurements are made by the use of the fluorescence intensity, so that the protein phosphatase activity can be measured with high sensitivity.

2) The reagents of the present invention can be stably stored for a long period of time, because they contain no radioactive phosphorus compounds.

3) The methods for measuring the activity according to the present invention are not based on the measurement of free phosphate, so that one containing phosphate can be used as the samples.

4) According to the present invention, the excitation wavelength in measuring the fluorescence intensity can be set to a wavelength different from the absorption wavelength of protein by appropriately selecting the fluorescent group. Therefore, crude extracts of tissues can also be used as the samples.

5) When the protein phosphatases to be measured are resistant to the proteases used for the measurement, which have the properties as described above, the dephosphorylation reaction of the substrate can be traced on real time.

---

What is claimed is:

1. A peptide derivative, which may be protected, containing a fluorescent group, a quenching group and a phosphoric acid group existing between said fluorescent group and said quenching group, in its molecule, the fluorescence in the fluorescent group being quenched with the quenching group.

2. The peptide derivative according to claim 1, wherein said peptide derivative is represented by general formula [1]:

$$A_1-X-A_2 \qquad [1]$$

wherein X represents an amino acid residue into which a phosphoric acid group is introduced; and $A_1$ and $A_2$ each represents an amino acid residue or a peptide chain which is bound to X and may be protected, one of $A_1$ and $A_2$ having a quenching group at its terminus or a side chain thereof, and the other having a fluorescent group at its terminus or a side chain thereof, the fluorescence in the fluorescent group being quenched with the quenching group in the molecule.

3. The peptide derivative according to claim 2, wherein said amino acid residue into which the phosphoric acid group is introduced is a phosphorylated hydroxyl group-containing amino acid residue.

4. The peptide derivative according to claim 2, wherein said amino acid residue into which the phosphoric acid group is introduced is a tyrosine residue, a serine residue or a threonine residue.

5. The peptide derivative according to claim 2, wherein the number of amino acid residues between the amino acid residue to which the quenching group is bound and the amino acid residue to which the fluorescent group is bound is 1 to 40.

6. The peptide derivative according to claim 2, wherein said peptide derivative is composed of 3 to 42 amino acid residues.

7. The peptide derivative according to claim 1, wherein the peptide derivative comprises an amino acid sequence represented by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13 or SEQ ID NO:14.

8. The peptide derivative according to claim 1, wherein the fluorescent group is a member selected from the group consisting of a (7-methoxy-coumarin-4-yl)acetyl group, a 5[(2-aminoethyl)amino]-naphthalene-1-sulfonic acid group and a 9,10-dioxa-syn-3,4,6,7-tetramethylbimane group.

9. The peptide derivative according to claim 1, wherein the quenching group is a member selected from the group consisting of a 4-(4-dimethylaminophenylazo)benzoyl group and a 4-(4-dimethylaminophenylazo)sulfonyl group.

10. The peptide derivative according to claim 1 which is any one of the following compounds:

Flu-Gly-Asp-Ala-Glu-pTyr-Ala-Ala-Lys(Inh)-Arg-NH$_2$,
Flu-Gly-Glu-Gly-Thr-pTyr-Gly-Lys(Inh)-Arg-NH$_2$,
Flu-Gly-Glu-Val-Asn-pTyr-Glu-Glu-Lys(Inh)-Arg-NH$_2$,
Flu-Gly-Glu-Pro-Gln-pTyr-Gln-Pro-Lys(Inh)-Arg-NH$_2$,
Flu-Gly-Glu-Lys-Glu-pTyr-His-Ala-Lys(Inh)-Arg-NH$_2$,
Flu-Gly-Asp-Gly-Val-pTyr-Ala-Ala-Lys(Inh)-Arg-NH$_2$,
Flu-Gly-Ser-Ala-pTyr-Gly-Lys(Inh)-Arg-NH$_2$,
Flu-Gly-Gly-Ser-pTyr-Ser-Lys(Inh)-Arg-NH$_2$,
Flu-Gly-Arg-Val-Phe-pSer-Lys(Inh)-Arg-NH$_2$,
Flu-Gly-Asp-Arg-Phe-pThr-Lys(Inh)-Arg-NH$_2$,
Flu-Gly-Arg-Lys-Phe-pThr-Lys(Inh)-Arg-NH$_2$,
Flu-Gly-Pro-Gly-Phe-pSer-Lys(Inh)-Arg-NH$_2$,
Flu-Gly-Thr-Arg-Phe-pSer-Lys(Inh)-Arg-NH$_2$, and
Flu-Gly-Lys-Arg-Phe-pSer-Lys(Inh)-Arg-NH$_2$ wherein Flu represents a fluorescent group, pTyr represents an O-phosphotyrosine residue, pSer represents an O-phosphoserine residue, pThr represents an O-phosphothreonine residue, Inh represents a quenching group, Lys(Inh) represents a lysine residue to which a quenching group is bound.

* * * * *

UNITED STATES PATENT AND TRADEMARK OFFICE
CERTIFICATE OF CORRECTION

PATENT NO. : 5,917,012

DATED : June 29, 1999

INVENTOR(S) : Makoto Nishikata

It is certified that error appears in the above-identified patent and that said Letters Patent is hereby corrected as shown below:

Cover page [30] Foreign Application Priority Data
  Replace "April 3, 1997" with --April 30, 1997--.

Signed and Sealed this

Ninth Day of November, 1999

Attest:

Attesting Officer

Q. TODD DICKINSON

Acting Commissioner of Patents and Trademarks